US012690784B2

(12) United States Patent
Chae et al.

(10) Patent No.: US 12,690,784 B2
(45) Date of Patent: Jul. 28, 2026

(54) APPLICATOR FOR CONTINUOUS BLOOD GLUCOSE MEASUREMENT DEVICE

(71) Applicant: I-SENS, INC., Seoul (KR)

(72) Inventors: Kyung Chul Chae, Seoul (KR); Hyun Ho Choi, Seoul (KR); Goang Yel Ryu, Seoul (KR); Ji Hoon Wang, Seoul (KR)

(73) Assignee: I-SENS, INC., Seoul (KR)

( * ) Notice: Subject to any disclaimer, the term of this patent is extended or adjusted under 35 U.S.C. 154(b) by 188 days.

(21) Appl. No.: 18/280,210

(22) PCT Filed: Nov. 9, 2021

(86) PCT No.: PCT/KR2021/016215
§ 371 (c)(1),
(2) Date: Sep. 2, 2023

(87) PCT Pub. No.: WO2022/186444
PCT Pub. Date: Sep. 9, 2022

(65) Prior Publication Data
US 2024/0138716 A1 May 2, 2024

(30) Foreign Application Priority Data
Mar. 4, 2021 (KR) ........................ 10-2021-0028534

(51) Int. Cl.
*A61B 5/1455* (2006.01)
*A61B 5/145* (2006.01)
(Continued)

(52) U.S. Cl.
CPC ...... *A61B 5/14532* (2013.01); *A61B 5/14503* (2013.01); *A61B 5/15113* (2013.01); *A61B 5/155* (2013.01)

(58) Field of Classification Search
CPC .......................... A61B 5/1455; A61B 5/14532
See application file for complete search history.

(56) References Cited

U.S. PATENT DOCUMENTS

| | | |
|---|---|---|
| 2007/0203966 A1 | 8/2007 | Brauker et al. |
| 2019/0350527 A1 | 11/2019 | Antonio et al. |
| 2020/0178899 A1* | 6/2020 | Chae ................... A61B 5/6848 |

FOREIGN PATENT DOCUMENTS

| | | |
|---|---|---|
| EP | 2 826 422 | 1/2015 |
| JP | 2014-158970 | 9/2014 |

(Continued)

OTHER PUBLICATIONS

International Search Report for PCT/KR2021/016215 mailed on May 30, 2022 and its English translation from WIPO (now published as WO 2022/186444).

(Continued)

*Primary Examiner* — Marjan Fardanesh

(74) *Attorney, Agent, or Firm* — WOMBLE BOND DICKINSON (US) LLP

(57) ABSTRACT

According to the present disclosure, an applicator for a continuous blood glucose measurement device, the applicator being operated by attaching a body attachment unit to the body of a user, the body attachment unit including a sensor member which is inserted into the body of the user in order to measure the blood glucose, comprises: a main case; a plunger to which the body attachment unit is detachably coupled and which is installed in the main case to be movable from a first position to a second position so that the body attachment unit can be discharged to the outer direction of the main case; a needle which is detachably coupled to the body attachment unit so as to be inserted into the body of the user along with the sensor member; and a needle separating unit which separates the needle from the body of the user by moving the needle in the direction opposite to the discharge direction of the plunger, wherein the needle separating unit includes a locking unit which can be assembled with the (Continued)

plunger in the manner of being engaged with one side of the plunger.

9 Claims, 15 Drawing Sheets

(51) Int. Cl.
    *A61B 5/151*         (2006.01)
    *A61B 5/155*         (2006.01)

(56)               References Cited

FOREIGN PATENT DOCUMENTS

| | | |
|---|---|---|
| JP | 2016-128031 | 7/2016 |
| JP | 2020-532326 | 12/2021 |
| JP | 2023-541266 | 9/2023 |
| KR | 10-2018-0132557 | 12/2018 |
| KR | 10-2020-0014001 | 2/2020 |
| KR | 10-2020-0014002 | 2/2020 |
| KR | 10-2020-0014156 | 2/2020 |

OTHER PUBLICATIONS

Written Opinion of the International Searching Authority for PCT/KR2021/016215 mailed on May 30, 2022 and its English translation from WIPO (now published as WO 2022/186444).

Office Action dated Jun. 24, 2025 for Japanese Patent Application No. 2023-552530 and its English translation provided by Applicant's foreign counsel.

Extended European Search Report dated Dec. 12, 2024 for European Patent Application No. 21929306.5.

Office Action dated Aug. 16, 2024 for Korean Patent Application No. 10-2024-0091209 and its English translation from Global Dossier.

Notice of Allowance dated Nov. 4, 2025 for Japanese Patent Application No. 2023-552530 and its English translation provided by Applicant's foreign counsel.

Office Action (1st) dated Mar. 13, 2026 for Chinese Patent Application No. 202180094832.2 and its English translation provided by Applicant's foreign counsel.

Extended European Search Report dated May 13, 2026 for European Patent Application No. 26158355.3.

* cited by examiner

[Fig. 1]
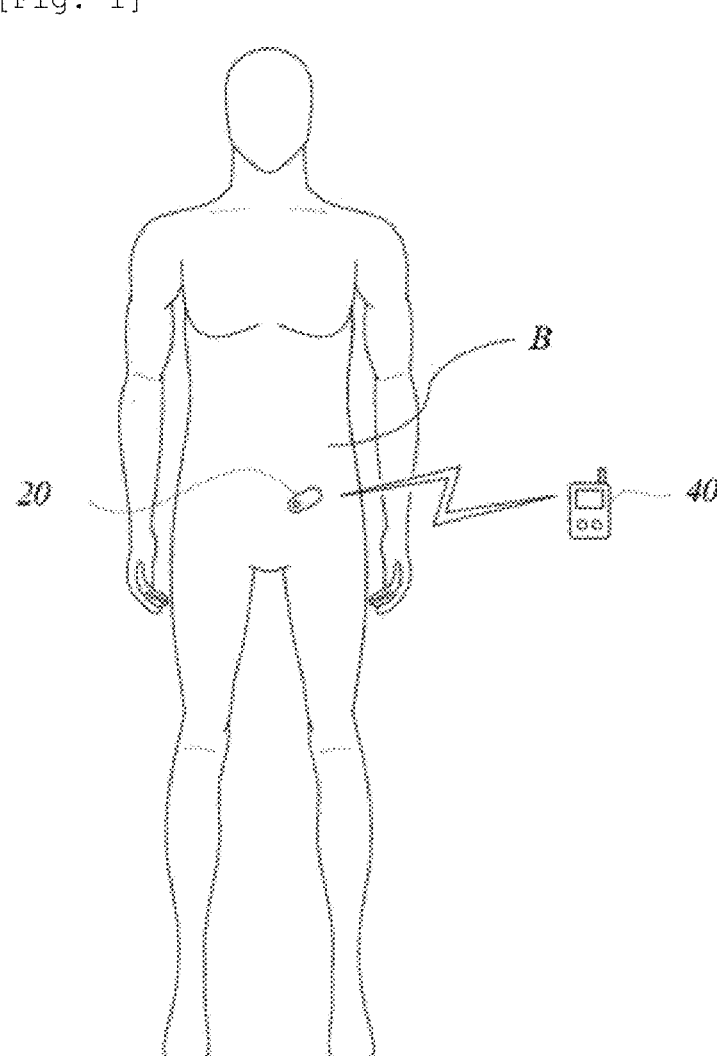

[Fig. 2]
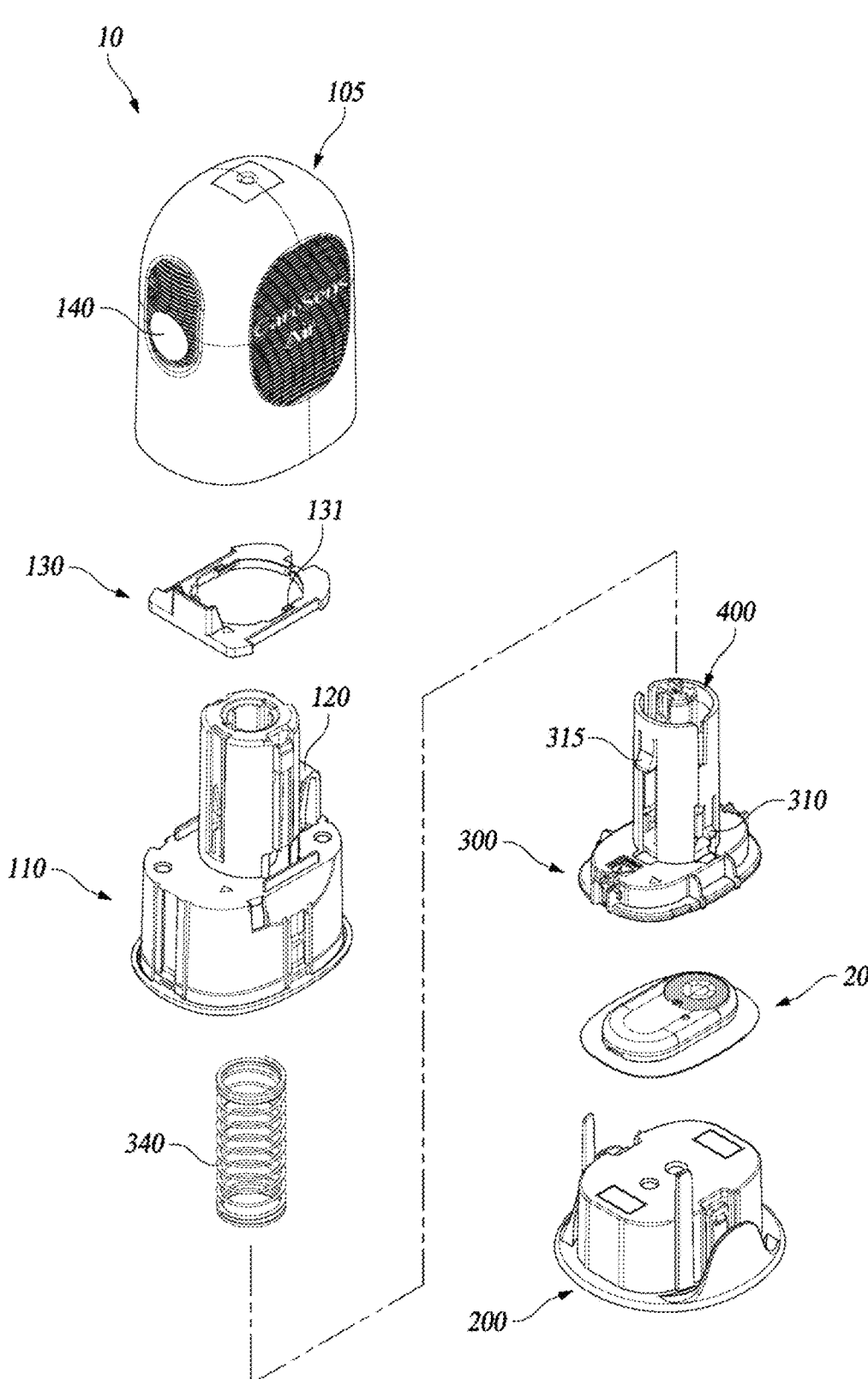

[Fig. 3]
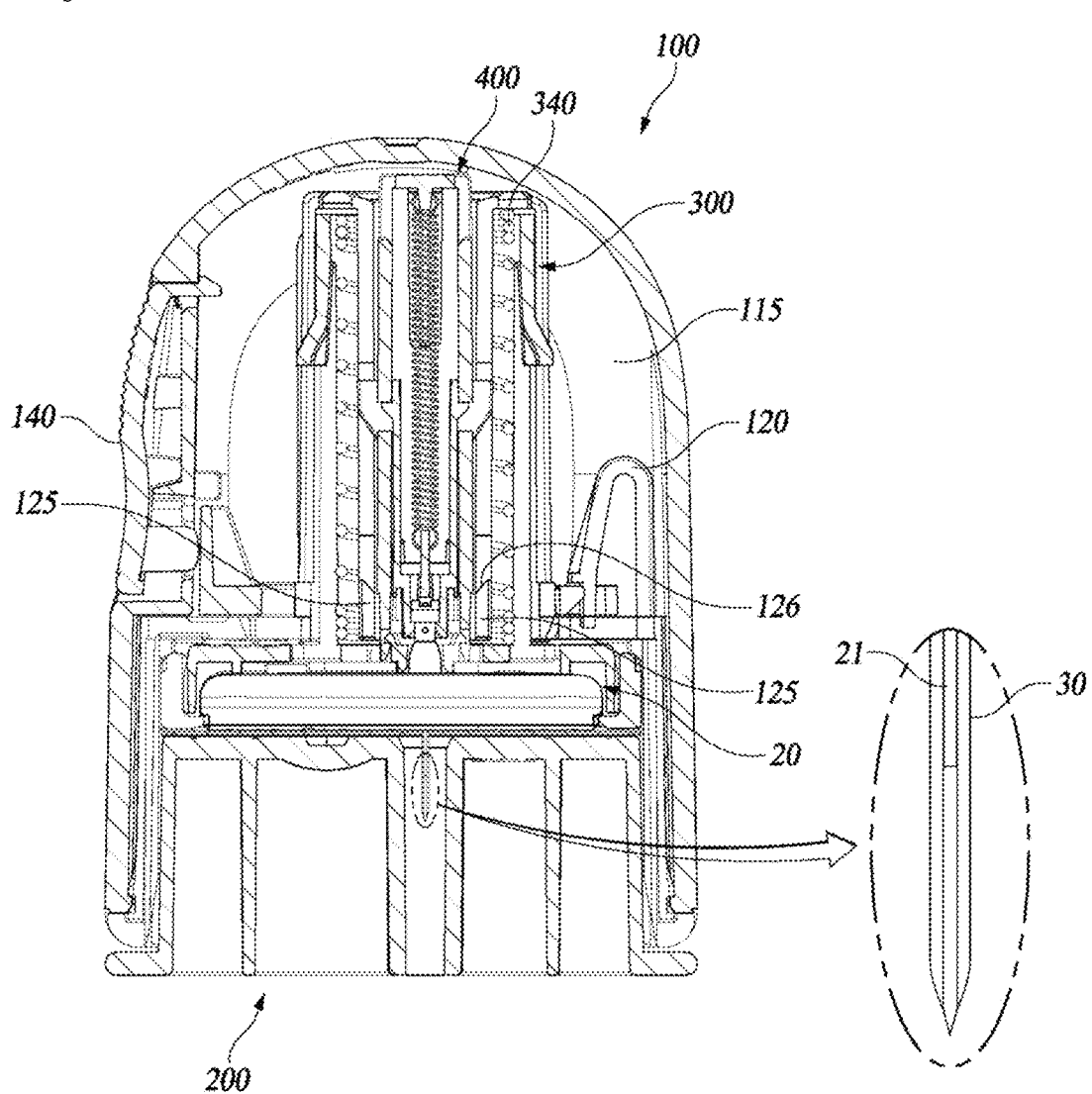

[Fig. 4]
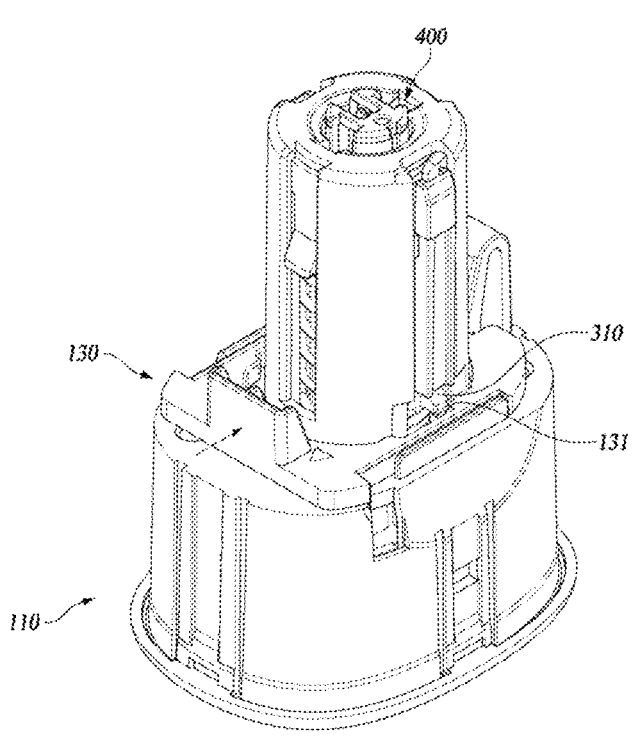
[Fig. 5]
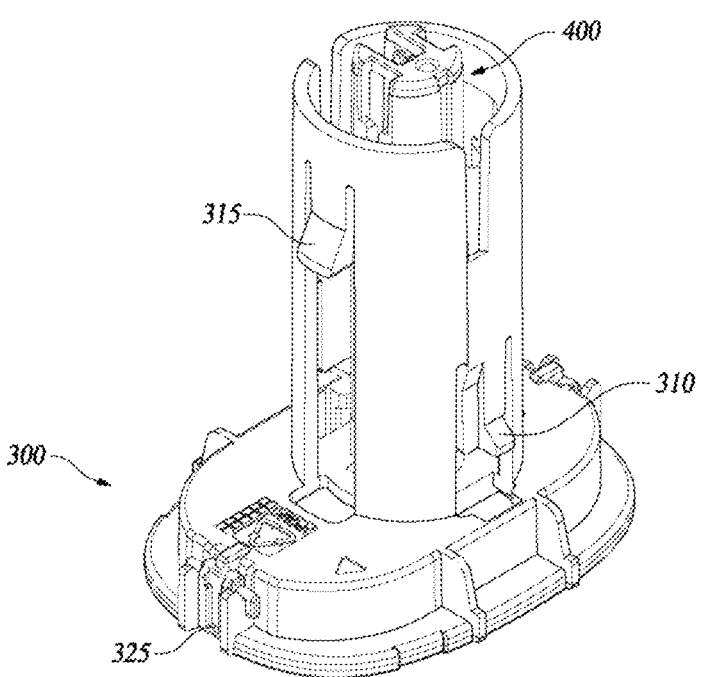

[Fig. 6]

[Fig. 7]
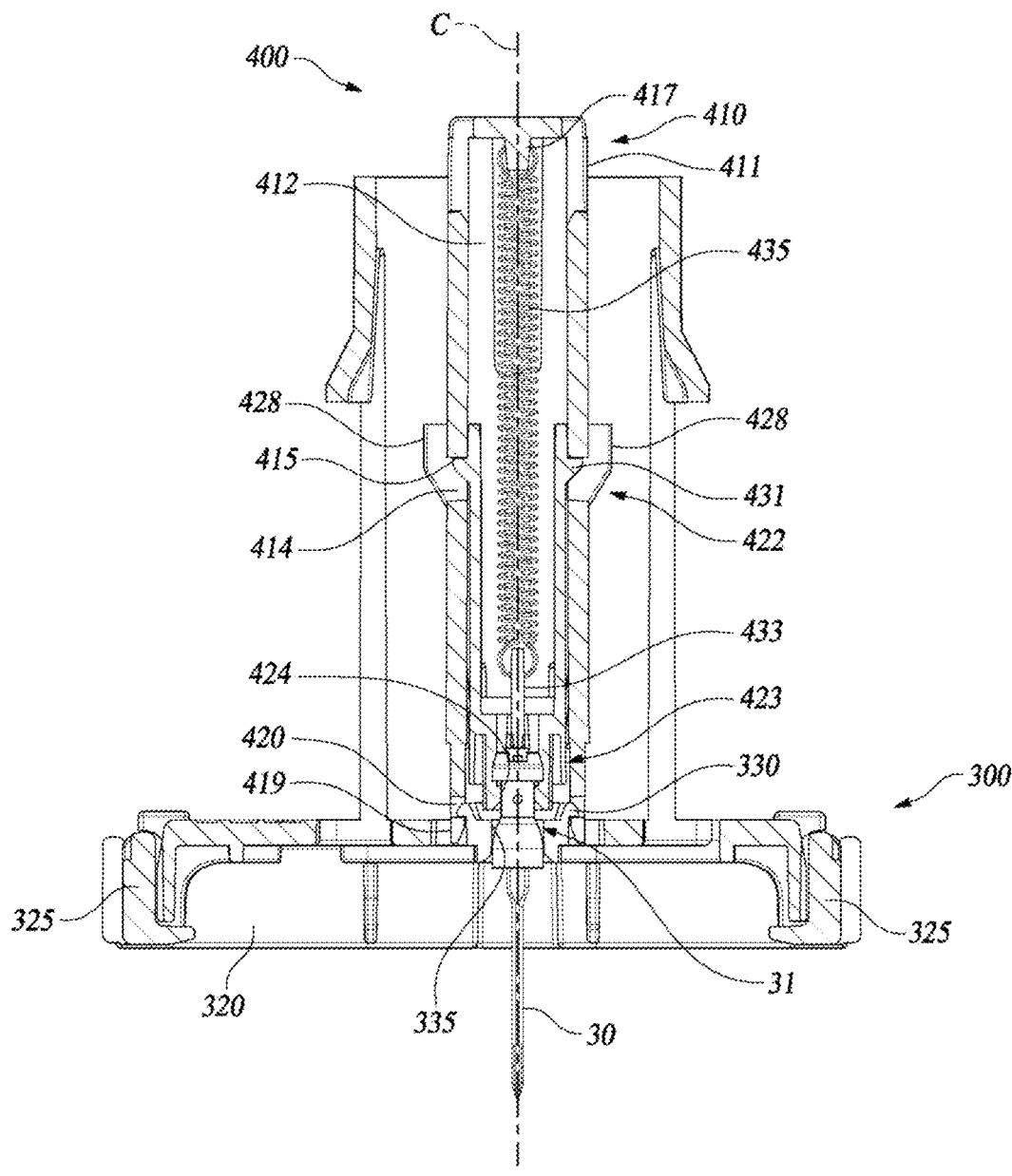

[Fig. 8]
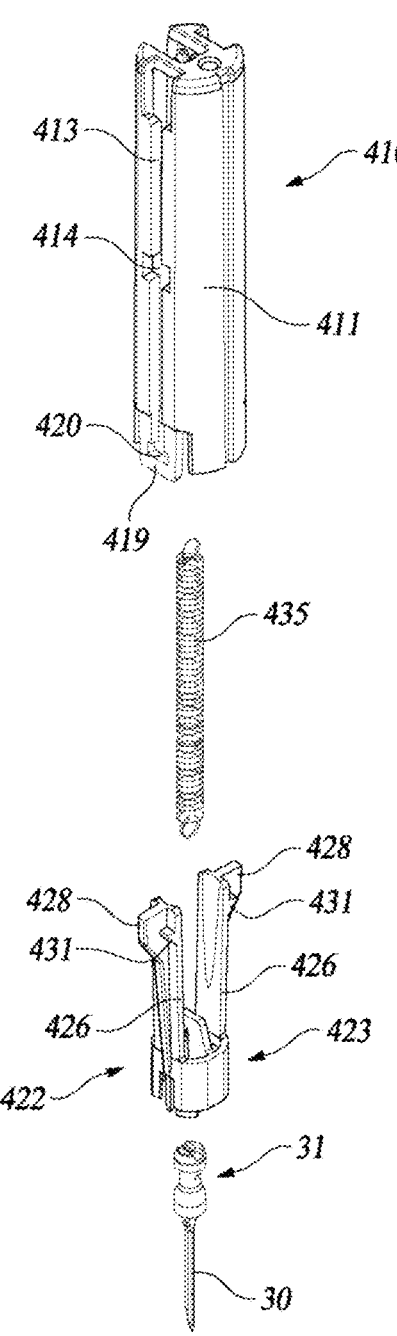

[Fig. 9]
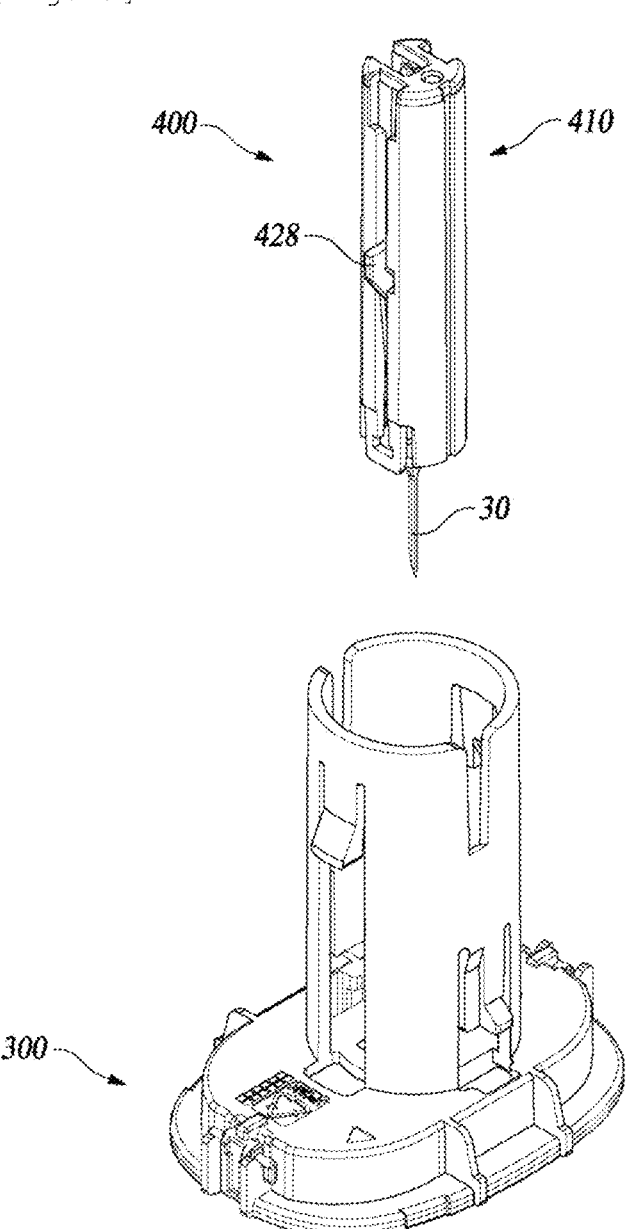

[Fig. 10]
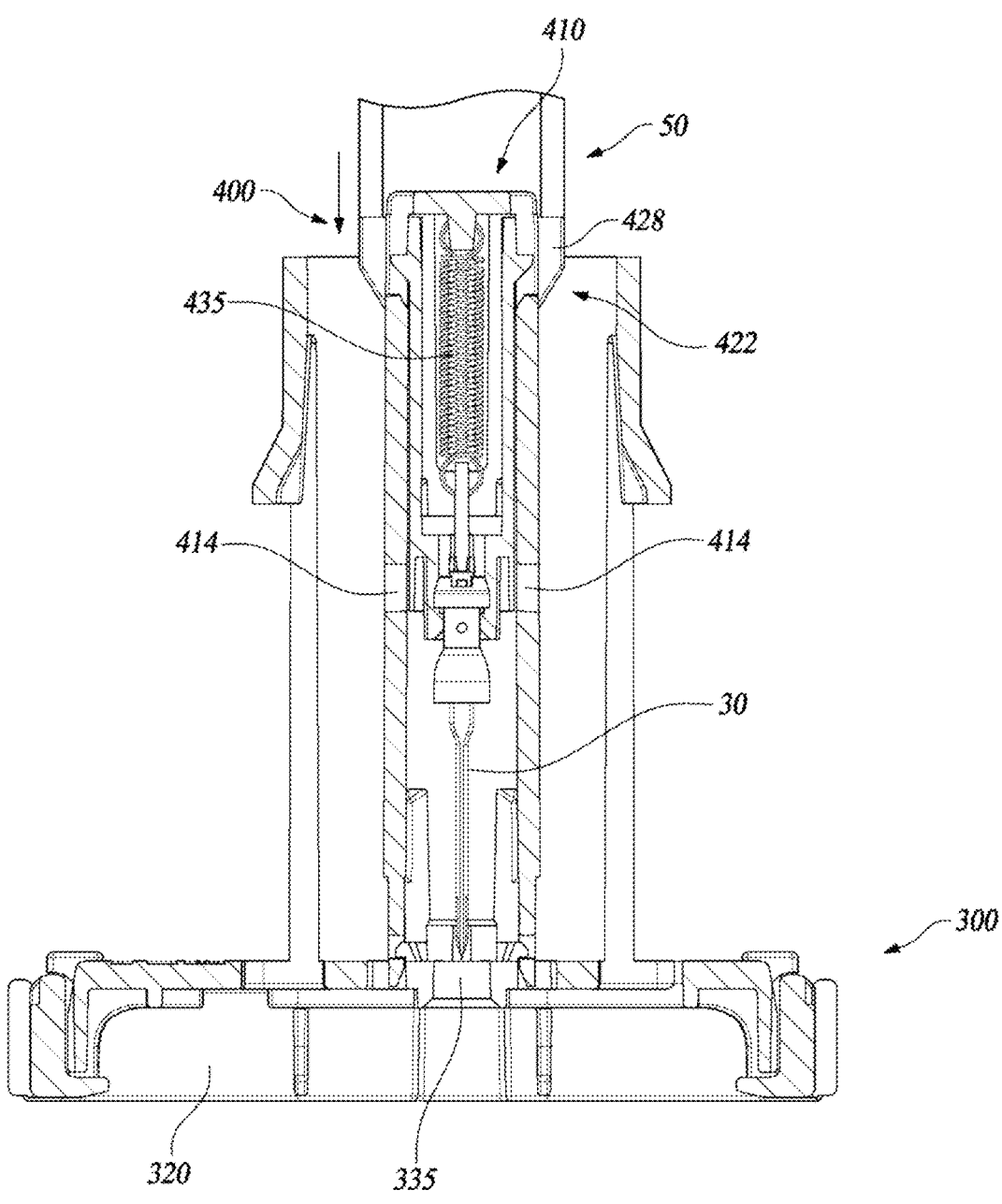

[Fig. 11]
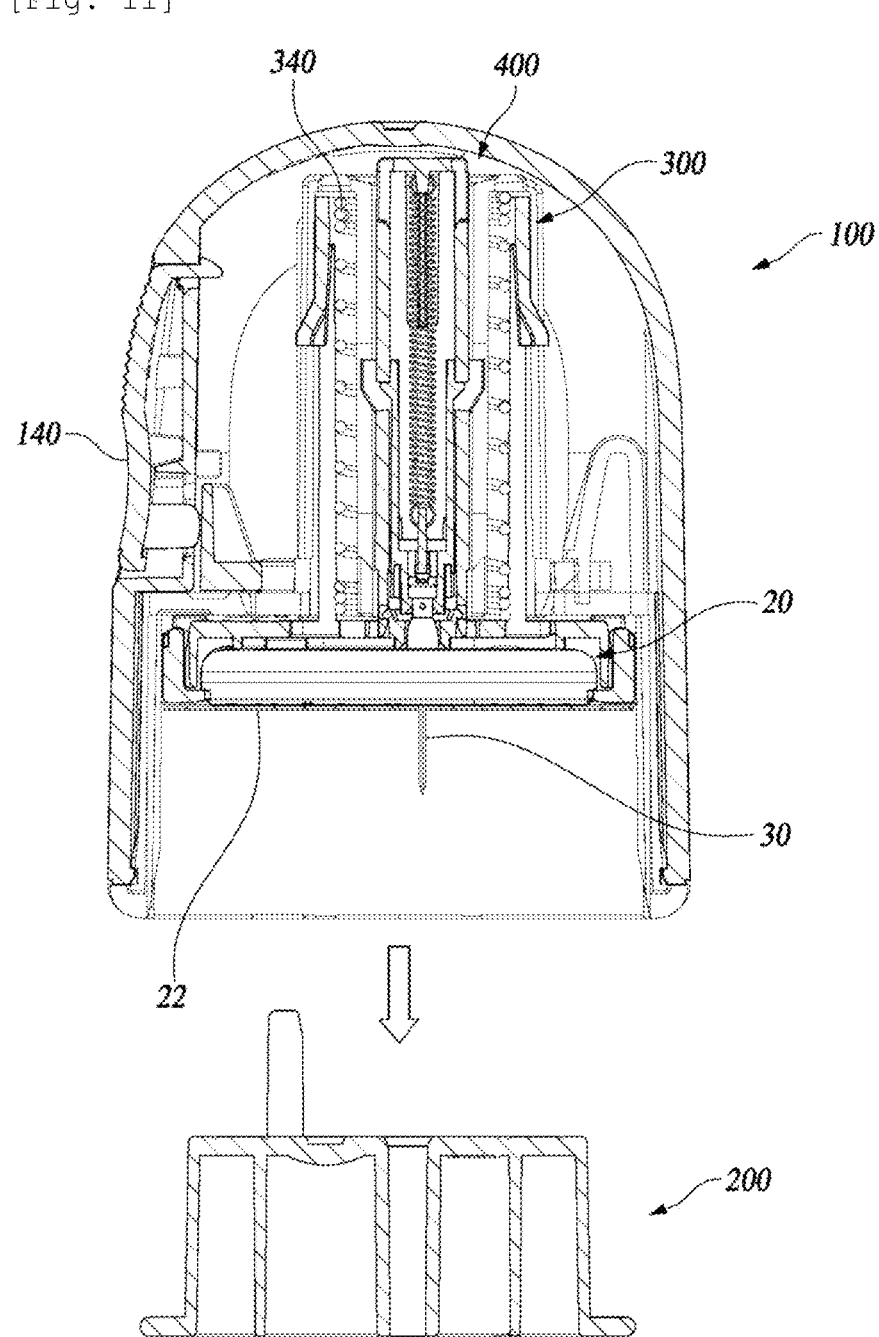

[Fig. 12]
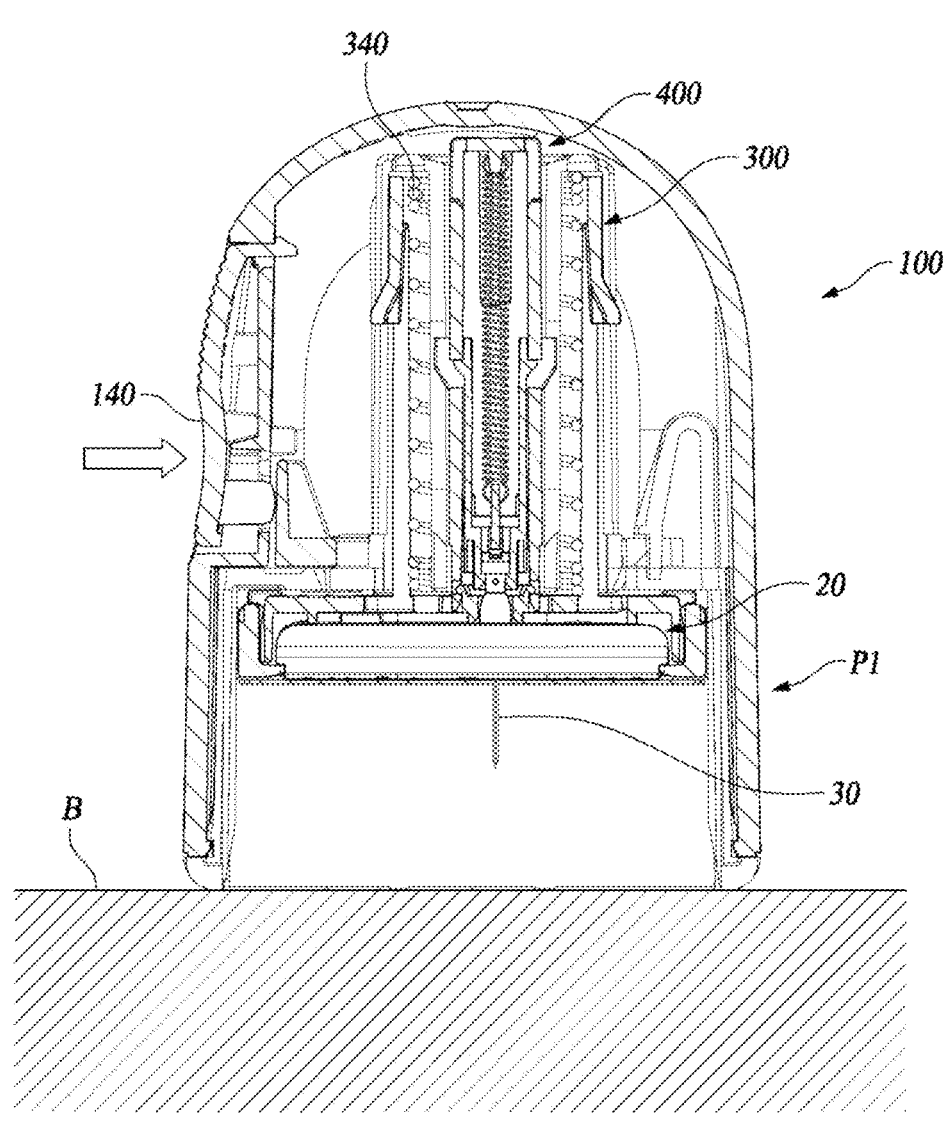

[Fig. 13]
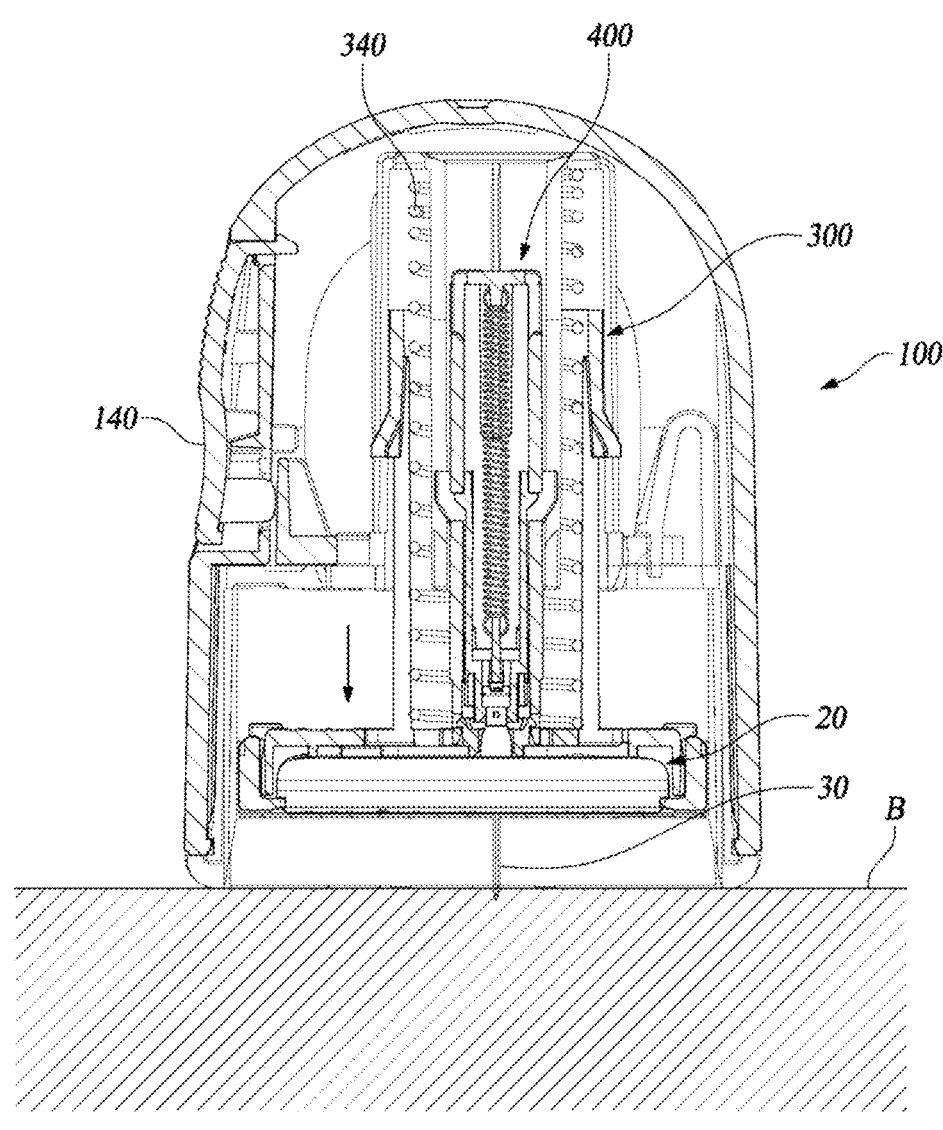

[Fig. 14]
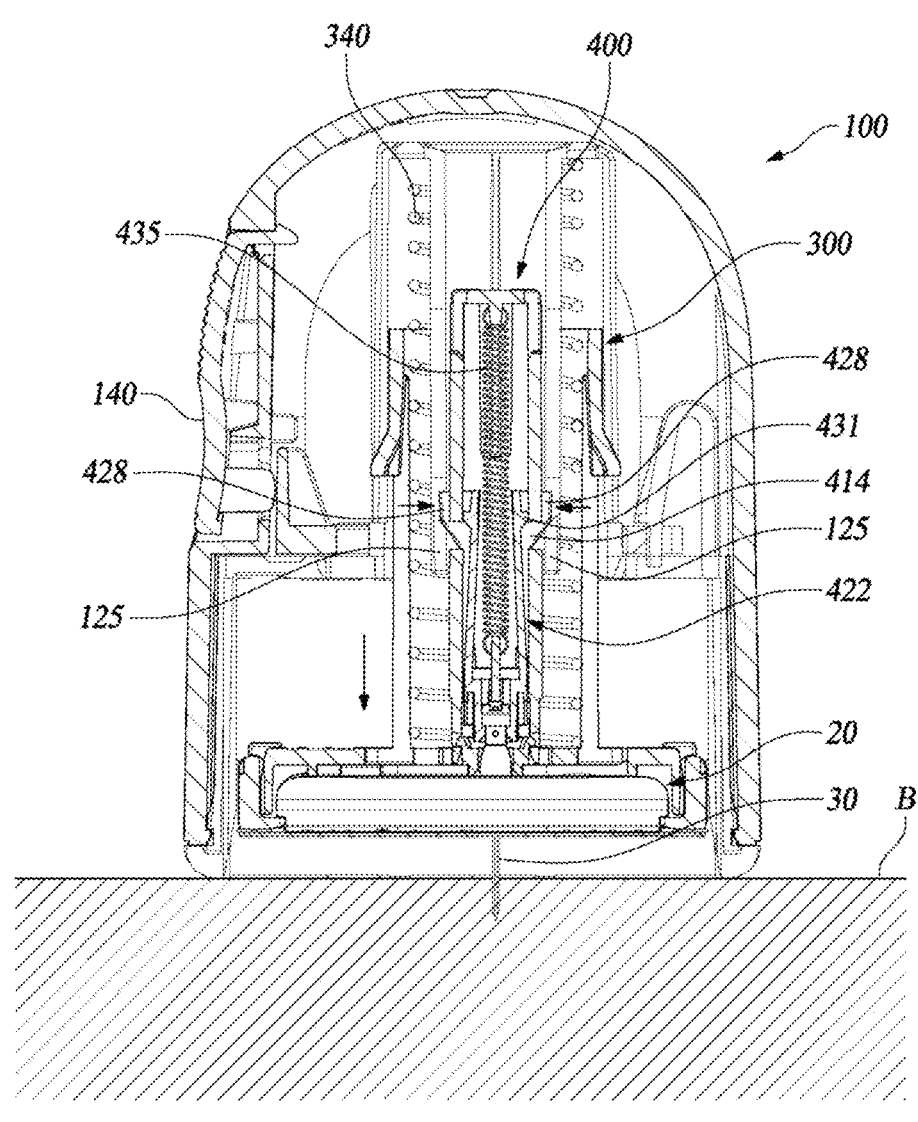

[Fig. 15]
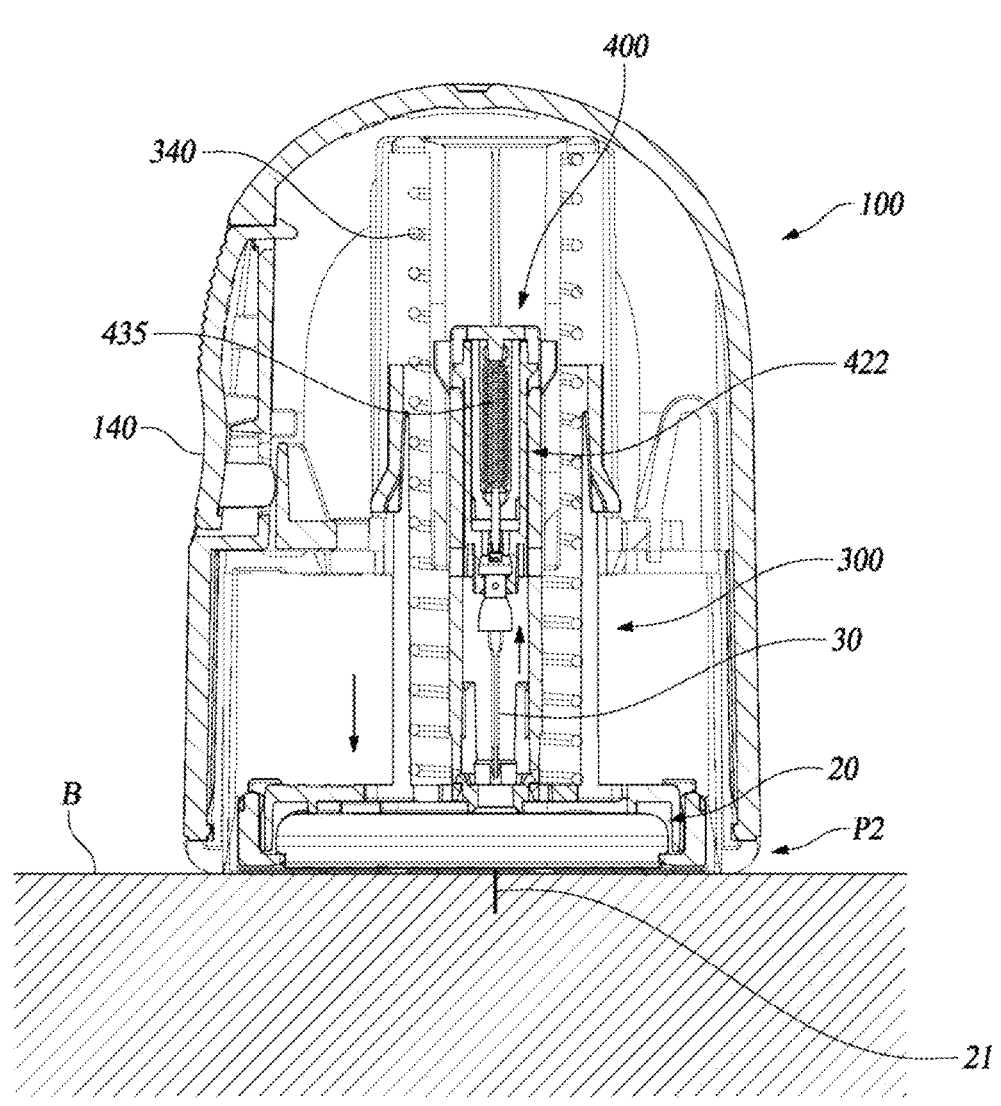

[Fig. 16]
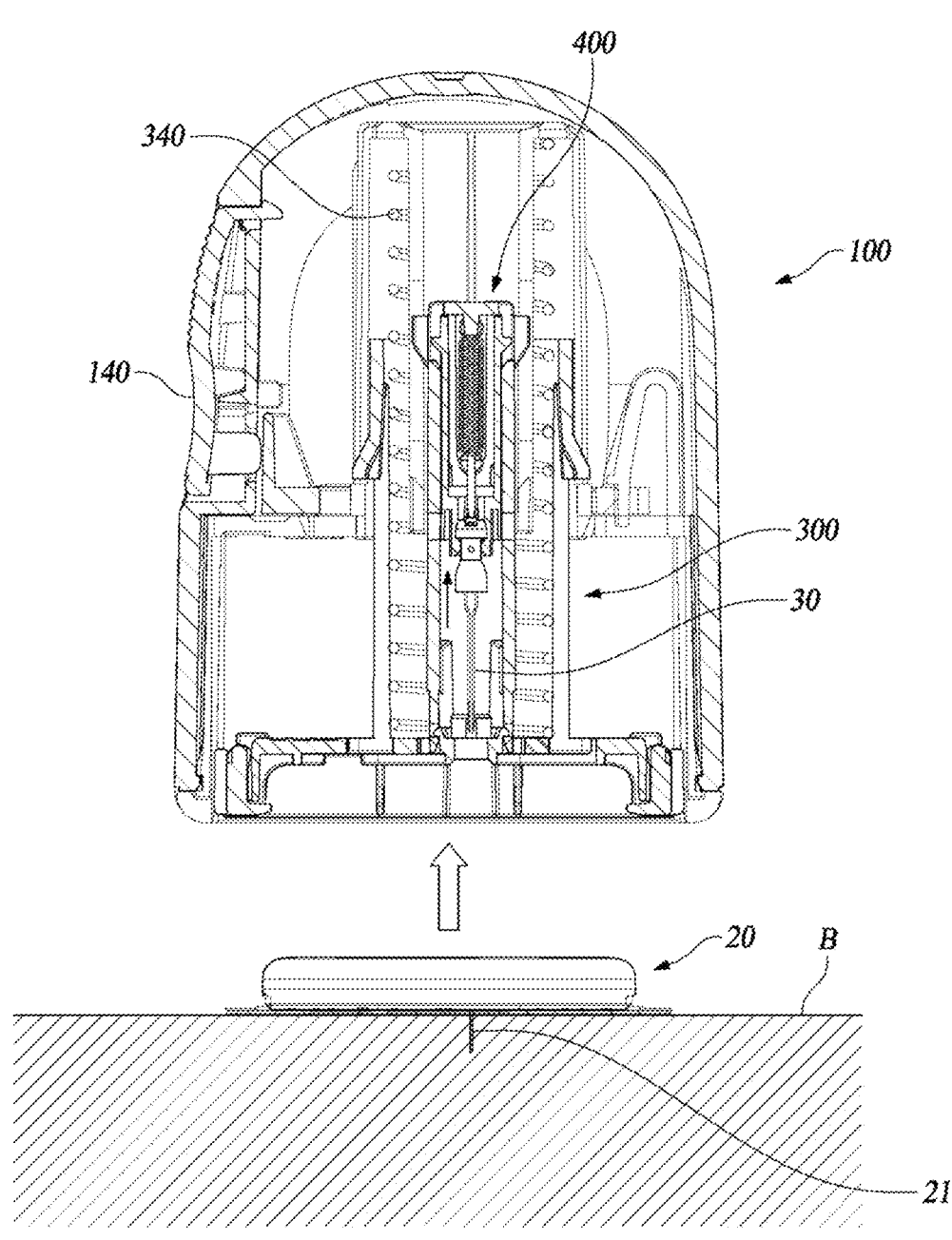

APPLICATOR FOR CONTINUOUS BLOOD GLUCOSE MEASUREMENT DEVICE

CROSS-REFERENCE TO RELATED APPLICATIONS

The present application is the U.S. National Phase of PCT Application No. PCT/KR2021/016215 filed on Nov. 9, 2021, which claims the priority to Korean Patent Application No. 10-2021-0028534 filed on Mar. 4, 2021, the entire contents of which are incorporated herein by reference.

TECHNICAL FIELD

The present disclosure relates to an applicator for a continuous blood glucose measurement apparatus, and, more specifically, relates to an applicator for a continuous blood glucose measurement apparatus for attaching a body attachable unit attached to a user's body to measure blood glucose and transmit measurement information to an outside.

BACKGROUND

Diabetes is a chronic medical condition that is common in modern people. Diabetes is caused by an absolute increase of the sugar level in the blood by failing to correct the balance of sugar in the blood, which is cause by absolute deficiency or relative insufficiency of insulin, produced by the pancreas, due to various reasons such as obesity, stress, poor eating habits, and inherited hereditary factors.

The blood usually contains a certain concentration of glucose, and tissue cells gain energy from the glucose.

However, when the glucose is increased excessively more than needed, the glucose cannot be properly stored in the liver, muscle, or adipose tissue and is accumulated in the blood, because of this, patients with diabetes maintain a much higher blood glucose level than normal people. As excessive blood glucose passes through the tissues and is discharged into the urine, it results in deficiency of glucose, which is absolutely necessary for all tissues of the body, thereby causing abnormalities in respective body tissues.

Diabetes is characterized by absence of subjective symptoms at the beginning of the condition, when diabetes progresses, diabetes-specific symptoms such as overdrink, overeat, polyuria, weight loss, weariness, skin itchiness, and lower ability of naturally healing on injury on hands and feet are shown. Further progression of diabetes leads to complications such as visual disturbances, hypertension, kidney disease, paralysis, periodontal disease, muscle spasms and neuralgia, as well as gangrene.

In order to diagnose diabetes beforehand and manage to prevent the progression of diabetes into complications associated therewith, systematic blood glucose measurement and treatment should be performed.

For diabetes patients as well as people having higher than normal blood glucose, even though diabetes has not yet developed, medical device manufacturers offer a variety of blood glucose meters to measure blood glucose levels.

Glucose measuring devices may be categorized into a single time measurement type measuring a blood glucose level and collecting blood from a fingertip by a user every single time and a continuous measurement type attaching a glucose monitoring system to the belly or an arm of the user and continuously measuring blood glucose levels.

Diabetics patients generally experience hyperglycemia and hypoglycemia, an emergency may occur in the hypoglycemic conditions, and the patients may become unconscious or die if a hypoglycemic condition lasts for an extended period of time without the supply of sugar. Accordingly, although rapid discovery of the hypoglycemic condition is critically important for diabetics, blood-collecting type glucose monitoring devices intermittently measuring glucose have limited ability to accurately detect it.

Recently, to overcome such a drawback, continuous glucose monitoring systems (CGMSs) inserted into the human body to measure a blood glucose level every few minutes have been developed. To minimize such pain and aversion caused by blood collection, a continuous glucose monitoring systems can continuously measure glucose levels by inserting a needle-shaped sensor into a portion of the human body, such as the belly or an arm, which is less pain sensitive.

A continuous glucose monitoring system includes a sensor module inserted and attached to the skin of the human body and measuring a blood glucose level by extracting body fluid, a transmitter transmitting the blood glucose level measured by the sensor module to a terminal, the terminal outputting the received blood glucose level, and any other appropriate component. The sensor module includes a needle-shaped sensor probe for insertion into subcutaneous fat to extract interstitial fluid and any other appropriate component. A separate applicator for attaching the sensor module to the body is used.

Those continuous glucose monitoring systems are manufactured to have a wide variety of types depending on their manufacturers, and are used in a variety of methods. However, most of the continuous glucose monitoring systems are manufactured and distributed as a type that a one-time use sensor module is attached to the human body using an applicator. The user must perform several steps for the operation of the applicator for attaching a one-time use sensor module to the body, and after attaching the sensor module to the body, various subsequent procedures, such as pulling out the needle by the user himself or herself, need to be performed.

For example, the single-use sensor module must be unpacked and inserted accurately in the applicator, and in a state in which the sensor module is inserted to the applicator, the sensor module needs to be inserted into the skin by manipulating the applicator. After the insertion, a manipulation, such as pulling out the needle inserted into the skin is required to be performed. In addition, in order to transmit blood glucose measurement results to the user terminal, there is an inconvenience in that a manipulation such as coupling a separate transmitter to the sensor module has to be performed.

In addition, the conventional applicator has a problem in that the assembly of the parts is cumbersome, the manufacturing time is long, and the automated production is difficult.

SUMMARY

Technical Problem

The purpose of the present disclosure, which has been made in view of the above points, is for providing an applicator for a continuous blood glucose measurement apparatus capable of making the assembly of parts easy and reducing manufacturing time and reducing manufacturing cost by automatic production.

Solution to Problem

To solve the problems described above, according to an embodiment of the present disclosure, an applicator for a continuous blood glucose measurement apparatus to operate to attach a body attachable unit having a sensor unit inserted into a body of a user for measuring blood glucose comprises: a main case; a plunger separatably coupled to the body attachable unit, and installed to be movable from a first location to a second location inside the main case to discharge the body attachable unit in a direction of an outside of the main case; a needle separatably coupled to the body attachable unit to be inserted into the body of the user together with the sensor unit; and a needle separation unit configured to move the needle in a direction opposite to a discharged direction of the plunger to separate the needle from the body of the user, wherein the needle separation unit comprises a locking part, and the locking part is configured to be assembled to the plunger in a way in which the locking part engages with one side of the plunger.

The needle separation unit may comprise: a support column having the locking part, a needle holder movably coupled to the support column to be coupled to one end of the needle, and a needle separation spring configured to apply an elastic force to the needle holder in a direction of separating the needle from the body of the user, and the support column may be configured to be assembled to the plunger by forming an assembly together with the needle holder and the needle separation spring.

The support column may comprise a body portion to which the needle holder and the needle separation spring are coupled, and the locking part may be provided at one end of the body portion.

The locking part may be elastically and deformably connected to the body portion.

The plunger may comprise a fixing part configured to be engageable with the locking part, and one of the locking part and the fixing part may have a coupling groove, and a remaining one of the locking part and the fixing part may have a fixing protrusion configured to be insertable into the coupling groove.

A support column hook to which one end of the needle separation spring is connected may be provided inside the support column, the needle holder may comprise a needle holder hook to which another end of the needle separation spring is connected, and the needle separation spring may be configured to apply the elastic force to the needle holder so that the needle holder is pulled toward the support column hook.

The needle holder may comprise: a holder head to which one end of the needle is coupled; a holder wing comprising a wing body elastically and deformably connected to the holder head and a stopper protruding from the wing body, the support column may comprise a snagging protuberance with which the stopper is engageable, and a pressing portion configured to elastically deform the holder wing such that the stopper is disengaged from the snagging protuberance may be provided inside the main case.

The holder wing may protrude from the wing body and includes a trigger in which a protruded height from the wing body is greater than a height of the stopper protruded from the wing body, the support column may comprise a slit formed in a longitudinal direction of the support column to allow the trigger to be inserted, and the pressing portion may be arranged on a movement path of the needle holder to elastically deform the holder wing by pressing the trigger while the plunger moves from the first location to the second location.

The needle separation unit may be configured to be assembled to the plunger in an elastically deformed state such that the needle separation spring applies the elastic force to the needle holder.

The needle separation unit may be configured to be assembled to the plunger in a state in which the needle separation spring is not elastically deformed.

Advantageous Effects of Invention

In an applicator according to an embodiment of the present disclosure, parts constituting a needle separation unit for separating a needle inserted into a user's body can form one single assembly to be coupled to a plunger to which a body attachment unit is mounted. Accordingly, it is easy to install components such as a needle holder and a needle separation spring constituting the needle separation unit. And, because the assembly process of coupling the assembled needle separation unit to the plunger can be automated, manufacturing time and cost can be reduced.

Additionally, because an applicator according to an embodiment of the present disclosure can be coupled to a plunger in a state in which a needle separation unit is assembled, during the manufacturing, it is easy for an operator to check that a needle holder and a needle release spring are installed in a state in which the needle can be removed. Therefore, it is possible to prevent a problem in which the applicator is shipped from a factory in an inoperable state.

BRIEF DESCRIPTION OF THE DRAWINGS

FIG. 1 shows a use example of a continuous blood glucose measurement apparatus.

FIG. 2 is an exploded perspective view for showing an applicator for a continuous blood glucose measurement apparatus according to an embodiment of the present disclosure.

FIG. 3 is a cross-sectional view for showing a state in which the body attachable unit is mounted on the applicator for a continuous blood glucose measurement apparatus according to an embodiment of the present disclosure.

FIG. 4 is a view for explaining an operation of a shooting plate provided in an applicator for a continuous blood glucose measurement apparatus according to an embodiment of the present disclosure.

FIGS. 5 and 6 are perspective views for illustrating an assembly of a plunger and a needle separating unit of an applicator for a continuous blood glucose measurement apparatus according to an embodiment of the present disclosure.

FIG. 7 is a cross-sectional view for showing an assembly of a plunger and a needle separating unit of an applicator for a continuous blood glucose measurement apparatus according to an embodiment of the present disclosure.

FIG. 8 is an exploded perspective view for illustrating a needle separating unit provided in an applicator for a continuous blood glucose measurement apparatus according to an embodiment of the present disclosure.

FIGS. 9 and 10 are views for explaining a process of assembling a plunger and a needle separating unit of an applicator for a continuous blood glucose measurement apparatus according to an embodiment of the present disclosure.

FIGS. 11 to 16 illustrate processes of attaching a body attachment unit to a user's body using an applicator for a continuous blood glucose measurement apparatus according to an embodiment of the present disclosure.

DETAILED DESCRIPTION OF EMBODIMENTS

Hereinafter, an applicator for a continuous blood glucose measurement apparatus according to the present disclosure will be described in detail with reference to the accompanying drawings.

FIG. 1 shows a use example of a continuous blood glucose measurement apparatus, FIG. 2 is an exploded perspective view showing an applicator for a continuous blood glucose measurement apparatus according to an embodiment of the present disclosure, and FIG. 3 is a cross-sectional view showing a state in which the body attachable unit is mounted on the applicator for a continuous blood glucose measurement apparatus according to an embodiment of the present disclosure.

The applicator(10) for a continuous blood glucose measurement apparatus according to an embodiment of the present disclosure is for attaching the body attachable unit (20) for measuring blood sugar to the body(B).

As shown in FIG. 1, the body attachable unit(20) is attached to the body(B) by the applicator(10), and the body attachable unit(20) periodically measures blood sugar from the body(B) and wirelessly transmits the measurement data to the external terminal(40). The body attachable unit(20) includes a sensor unit(21) partially inserted into the body, a wireless communication chip for wireless communication with the external terminal(40), and a battery. Since this body attachable unit(20) is disclosed in Korean Patent Publication No. 2020-0127097 and so on, a detailed description thereof will be omitted.

The applicator(10) according to an embodiment of the present disclosure has a structure in which the body attachable unit(20) can be installed therein. The applicator(10) can be operated by a user's manipulation to eject the body attachable unit(20) to the outside. The body attachable unit(20) can be attached to the body(B) by being mounted inside the applicator(10) and discharged from the applicator(10) according to the operation of the applicator(10).

The applicator(10) according to an embodiment of the present disclosure may be supplied to the user with the body attachable unit(20) mounted therein, but the present disclosure is not limited to this configuration.

An adhesive tape(22) is provided on one side of the body attachable unit(20) so that the body attachable unit(20) can be attached to the user's body(B) by the adhesive tape(22). The body attachable unit(20) may be mounted on the applicator(10) in a state where the adhesive tape(22) is covered with a release paper. A part of the release paper may be attached to the protective cap(200) of applicator(10) so that the release paper can be removed when the protective cap(200) is separated from the main case(100).

The applicator(10) may have a structure in which the body attachable unit(20) is fixed in an installed state and releases the fixing force to the body attachable unit(20) in a state in which the body attachable unit(20) is ejected. In a state where the body attachable unit(20) is mounted inside the applicator(10), the body attachable unit(20) may remain fixed to the applicator(10). When the body attachable unit (20) is discharged from the applicator(10), the body attachable unit (20) is separated from the applicator(10) and remains attached to the user's body(B).

The needle(30) can be detachably coupled to the body attachable unit(20) so that the sensor unit(21) can be stably inserted into the user's body(B), while the body attachable unit(20) is discharged from the applicator(10). The needle (30) surrounds one end of the sensor unit(21) so that one end of the sensor unit(21) can be stably inserted into the body(B) with the needle(30).

The needle(30) is coupled to the body attachable unit(20) so as to pass through the body attachable unit(20) in the thickness direction. One end of the needle(30) is made of a pointed shape so that it can be smoothly inserted into the user's body(B) by piercing the skin of the user's body(B), and the needle head (31) is provided at the other end of the needle(30). When the body attachable unit(20) is ejected from the applicator(10), the needle(30) penetrates the skin of the user's body(B) before the sensor unit(21) so that the needle(30) plays a role in assisting the sensor unit(21) to stably insert into the body(B). After the body attachable unit(20) is attached to the user's body B, the needle(30) may be separated from the user's body(B) by the needle separation unit(400) of the applicator(10).

Hereinafter, a detailed configuration of the applicator(10) according to an embodiment of the present disclosure will be described in more detail.

The applicator(10) according to an embodiment of the present disclosure includes a main case(100) which has a press button(140) at one side of the main case(100) so as to be pressed by a user, a plunger(300) supporting the body attachable unit(20) and movably installed inside the main case(100), the plunger spring(340) applying an elastic force to the plunger(300), and a needle separation unit(400) for separating the needle(30) coupled to the body attachable unit(20) from the body attachable unit(20). The plunger (300) may move from the first position(P1) inside the main case(100) to the second position(P2) to eject the body attachable unit(20) outward. A protective cap(200) for protecting the body attachable unit(20) inside the main case (100) is detachably coupled to one end of the main case (100).

While the body attachable unit(20) is coupled to the plunger(300), the protective cap(200) is coupled to the main case(100) to prevent the body attachable unit(20) from being exposed to the outside. The user can attach the body attachable unit(20) to the body(B) by operating the applicator(10) only after removing the protective cap(200).

The protective cap(200) not only protects the body attachable unit(20) inserted into the main case(100) from being exposed to the outside, but also supports the body attachable unit(20). The protective cap(200) can improve overall structural stability of the applicator(10) by being coupled to the main case(100).

The main case(100) includes an outer case(105) to which a press button(140) is mounted on one side, and an inner case(110) coupled to the inside of the outer case(105) to guide the linear movement path of the plunger(300). An accommodation space(115) is formed inside the main case (100) to accommodate the plunger(300), the needle separation unit(400), and the body attachable unit(20). The accommodation space(115) is open to the outside and the body attachable unit(20) may be discharged to the outside through this open portion of the accommodation space(115). The open portion of the accommodation space(115) may be opened and closed by the protective cap(200).

The press button(140) may be operated when a user presses it. Inside the main case(100), a shooting plate(130) that moves according to an operation of the press button (140) is movably installed.

The shooting plate(130) may move while being seated and supported on the inner case(110). The shooting plate (130) may slide according to an operation of the press button(140). The plunger(300) may be engaged with the shooting plate(130) at the first position(P1) and disengaged from the shooting plate(130) according to the movement of the shooting plate(130). When the plunger(300) is disengaged from the shooting plate(130), the plunger(300) may move to the second position(P2) by the elastic force of the plunger spring(340).

In addition to the press manipulation method as shown in the drawings, the press button(140) may be changed into various other structures capable of operating the shooting plate(130) according to a user's operation.

As shown in FIG. 4, on one side of the shooting plate (130), a base unit(131) into which the engaging hook(310) of the plunger(300) can engage is provided. The plunger (300) may be fixed at the first position(P1) when the engagement hook(310) is hooked on the base unit(131). When the shooting plate(130) is moved by the press button (140), the engagement hook(310) is released from the fulcrum(131), and the plunger(300) can move to the second position(P2).

The specific shape of the shooting plate(130) or the engagement structure between the shooting plate (130) and the plunger(300) are not limited to those shown and can be variously changed.

The inner case(110) includes a return unit(120) that elastically supports the shooting plate(130). The return unit (120) applies an elastic force to the shooting plate(130) in a direction opposite to the pressing direction by the press button(140) The member applies an elastic force in a direction opposite to the pressing direction by the button 140. Since the shooting plate(130) is supported by the return unit(120), the shooting plate(130) can maintain a stable engagement state with the engagement hook(310) of the plunger(300).

The plunger(300) may be installed inside the main case (100) to support the body attachable unit(20). The plunger (300) may discharge the body attachable unit(20) from the main case(100) by moving from the first position(P1) to the second position(P2) by the elastic force of the plunger spring(340). The plunger(300) includes a plunger protrusion (315). The plunger protrusion(315) limits the movement range of the plunger(300). When the plunger(300) moves to the second position(P2), the movement of the plunger(300) may be limited in such a way that the plunger protrusion (315) is engaged with one side of the inner case(110). Accordingly, the plunger(300) stops moving only to the second position P2 by the elastic force of the plunger spring(340) and does not leave the main case(100).

One end of the plunger(300) is formed with a sensor accommodation part(320) into which the body attachable unit(20) is inserted. The body attachable unit(20) is mounted on the sensor accommodation part(320) and can move from the first position(P1) to the second position(P2) together with the plunger(300). When the plunger(300) and the body attachable unit(20) move to the second position P2, the sensor unit(21) of the body attachable unit(20) may be inserted into the user's body(B).

A fixing hook(325) for fixing the body attachable unit(20) by engaging with the edge of the body attachable unit(20) inserted into the sensor accommodation part(320) is provided at an edge of the sensor accommodation part(320). The fixing hook(325) is rotatably coupled to the plunger (300), and can fix the body attachable unit(20) by engaging with the edge of the body attachable unit(20) in a state where the plunger(300) is positioned at the first position(P1). In addition, the fixing hook(325) can be disengaged from the body attachable unit(20) when the user separates the applicator(10) from the body attachable unit(20) attached to the user's body(B) in a state in which the plunger(300) is moved to the second position(P2).

In addition, a through-hole(335) through which the needle (30) can pass is formed in the plunger(300). The through-hole(335) is provided inside the plunger(300) so as to be connected to the sensor accommodation part(320). The needle(30) may pass through the through-hole(335) and be coupled to the body attachable unit(20) mounted on the sensor accommodation part(320).

Figure 6:
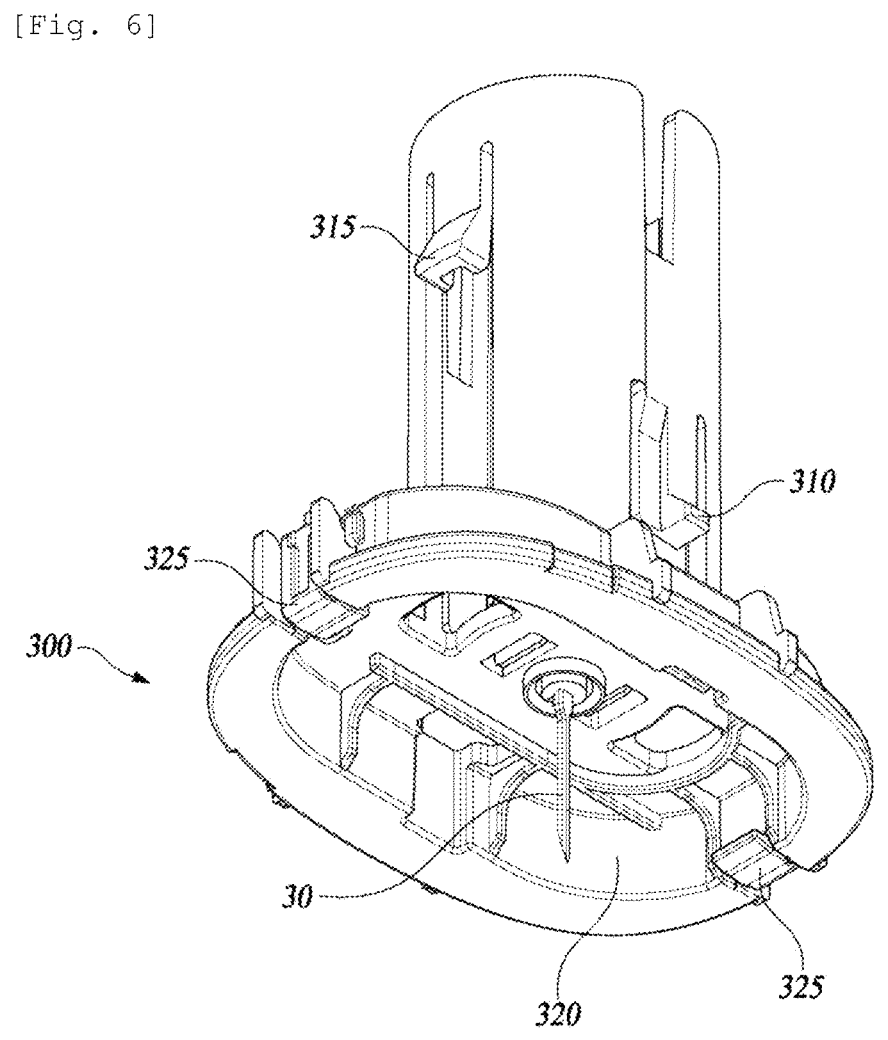

Referring to FIGS. 5 to 10, the needle separation unit (400) separates the needle(30) coupled to the body attachable unit(20) from the user's body(B) as the body attachable unit(20) moves from the first position(P1) to the second position(P2). The needle separation unit(400) includes a support column(410) which is fixed to the plunger(300), a needle holder(422) which is movably installed on the support column(410) and coupled to the needle head(31), and a needle separation spring(435) that elastically supports needle holder(422).

The support column(410) includes a body portion(411) in which an installation space(412) accommodating the needle holder(422) and the needle separation spring(435) is formed, and a locking part(419) provided at one end of the body portion(411).

Slits(413) for guiding the needle holder(422) are formed on both sides of the body portion(411). The slit(413) extends in the longitudinal direction of the body portion(411). A locking groove (414) into which the stopper(431) of the needle holder(422) can be inserted is formed in the middle of the slit(413). A snagging protuberance(415) on which the stopper(431) can be hung is provided inside the locking groove(414). A support column hook(417) to which the needle separation spring(435) is connected is provided inside the other end of the body portion(411).

A pair of the locking part(419) is provided at one end of the body portion(411) so as to face each other. The locking part(419) is formed in the shape of an elastically deformable plate. A coupling groove(420) is formed in the locking part(419). The support column(410) may be fixed to the plunger 300 in such a way that a pair of locking parts(419) are engaged with a fixing part(330) provided inside the plunger(300). The fixing part(330) includes a fixing protrusion(331) inserted into the coupling groove(420)

The support column(410) may be simply coupled to the plunger(300) in a manner in which a pair of locking parts (419) are engaged with the fixing part(330) of the plunger (300). Accordingly, when manufacturing the applicator(10), the needle separation unit(400) may be assembled to the plunger(300) in such a way that separation unit(400) is simply inserted into the plunger(300).

The specific shape of the locking part(419) or the coupling structure with the plunger(300) can be variously changed. As another example, a coupling groove may be provided in the fixing part(330) of the plunger(300), and the locking part(419) may include a fixing protrusion that can be inserted into the coupling groove of the plunger(300).

In addition, the support column(410) may be coupled to the plunger(300) in a variety of ways other than a structure that the support column(410) coupled to the plunger (300) by a locking part(419) provided separately from the body portion(411).

In addition, the support column(410) may be changed to structures other than the structure in which the installation space(412) in which the needle holder(422) and the needle separation spring(435) are accommodated is formed inside, as shown in drawings. The support column(410) may be changed to various other structures in which the needle holder(422) is movably coupled and can support the needle separation spring(435).

The needle holder(422) includes a holder head(423) to which the needle head(31) is coupled, and a holder wing (426) which has an elastically deformable connection to the holder head(423)

An insertion groove(424) into which the needle head(31) is inserted is formed inside the holder head(423). The needle(30) may be coupled to the needle head(31) in such a way that the part of reduced thickness in the middle of the needle head(31) is inserted into the insertion groove(424). The needle(30) is not easily separated from the holder head(423) because when a portion of the needle head(31) is inserted into the insertion groove(424), the portion of the needle head(31) is caught on the holder head(423).

The holder wing(426) has a shape extending from one end of the holder head(423) and has elastically deformable connection to one end of the holder head(423). The holder wing(426) is obliquely connected to one end of the holder head(423). That is, the holder wing(426) gradually moves away from the imaginary center line(C) passing through the center of the insertion groove(424) as it moves away from the holder head(423). The holder wing(426) includes a wing body(427) which has an elastically deformable connection to one end of the holder head(423) and a trigger(428) and a stopper(431) which are protruding from the wing body(427).

The trigger(428) is provided at one end of the wing body(427) to protrude outward from the wing body(427). The trigger(428) may be inserted into the slit(413) of the support column(410) and move linearly along the slit(413). Since the trigger(428) is inserted into the slit(413) and guided by the slit (413), the needle holder(422) may move linearly while being more stably supported by the support column(410). The trigger passes through the slit(413), and partially protrudes from the outer surface of the support column(410). While the support column(410) moves from the first position(P1) to the second position(P2) together with the plunger(300), the trigger(428) may contact the pressing portion(125) provided on the inner case(110).

The pressing portion(125) is arranged on the moving path of the needle holder(422) so as to press the trigger(428). While the needle separation unit(400) moves from the first position(P1) to the second position(P2), the holder wing (426) may be elastically deformed as the pressing portion (125) contacts the trigger(428) and presses the trigger(428) toward the inside of the support column (410). The pressing portion(125) is provided with a pressing inclined portion (126) to which the trigger(428) comes into contact. The pressing inclined portion(126) has a downwardly inclined shape in the moving direction of the needle separation unit(400).

The trigger(428) is provided with a trigger inclined portion(429) corresponding to the pressing inclined portion (126). The trigger inclined portion(429) has a shape inclined in the same direction as the inclined direction of the pressing inclined portion(126). While the needle separation unit(400) is moving from the first position(P1) to the second position (P2), as the trigger inclined portion(429) moves in contact with the pressing inclined portion(126), the shock generated when the trigger(428) comes into contact with the pressing portion(125) is reduced, and the pressing force of the pressing portion(125) may be more smoothly transmitted to the trigger(428). In addition, since the pressing force of the pressing portion(125) is stably transmitted to the trigger (428), the holder wing(426) may be elastically deformed more stably.

The stopper(431) protrudes outward from the wing body (427). The direction in which the stopper(431) protrudes from the wing body(427) is the same as the direction in which the trigger(428) protrudes from the wing body(427). And, the height of the protrusion of the stopper (431) from the wing body(427) is lower than the height of the protrusion of the trigger(428) from the wing body(427). The stopper (431) may be inserted into the locking groove(414) of the support column(410) and caught on the snagging protuberance (415). As shown in FIG. 7, as the stopper(431) is caught on the snagging protuberance (415), the needle holder(422) may maintain a lowered state towards one end of the support column(410).

At this time, even if the elastic force of the needle separation spring(435) is applied to the needle holder(422), since the stopper(431) is caught on the snagging protuberance(415), the needle holder(422) cannot move in the direction in which the elastic force of the needle separation spring(435) acts.

The stoppers(431) may be provided on both sides of the trigger(428), but the number of stoppers(431) installed may be variously changed.

As shown in the drawings, a pair of holder wings(426) may be symmetrically provided on both sides of the holder head(423), but the number of holder wings 426 may be variously changed.

In addition, the needle holder(422) has a needle holder hook(433) to which the other end of the needle separation spring(435) is connected. The needle holder hook(433) may be connected to the holder head(423) so as to be positioned between the pair of holder wings(426).

The needle release spring(435) applies an elastic force to the needle holder(422) in the direction of separating the needle(30) from the body attachable unit(20). One end of the needle separation spring(435) is connected to the support column hook(417) of the support column(410), and the other end of the needle separation spring(435) is connected to the needle holder hook(433) of the needle holder(422). The needle separation spring(435) has a tension spring structure and can apply elastic force to pull the needle holder(422) toward the support column hook(417).

As shown in FIG. 9, the needle separation unit(400) may be coupled to the plunger(300) as the needle holder(422) and the needle separation spring(435) form one assembly together with the support column(410). That is, before the support column(410) is coupled to the plunger(300), the needle holder(422) and the needle separation spring(435) are assembled to the support column(410) to form one assembly. Since this support column(410) is coupled to the plunger (300), the needle holder(422) and the needle separation spring(435) may also be assembled to the plunger(300) together with the support column(410).

The needle(30) may be coupled to the body attachable unit(20) when the needle separation unit(400) is coupled to the plunger(300) while being coupled to the needle holder (422). As another example, the needle(30) may be coupled to the needle holder(422) while being coupled to the body attachable unit(20). In addition, the order of coupling the needle(30) and the body attachable unit(20) or the order of coupling the needle(30) and the needle separation unit(400) may be variously changed according to the manufacturing process of the applicator(10).

As such, in the applicator(10) according to an embodiment of the present disclosure, installation of the needle holder(422) and the needle separation spring(435) is easy by adopting a structure in which the needle holder(422) of the needle separation unit(400) and the needle separation spring (435) form one assembly together with the support column (410) and are coupled to the plunger(300). In addition, because the assembly process of coupling the assembled needle separation unit(400) to the plunger(300) can be automated, manufacturing time and cost can be reduced.

Further, since the applicator(10) according to one embodiment of the present disclosure can be coupled to the plunger (300) in a state in which the needle separation unit(400) is assembled, during the manufacturing, it is easy for the operator to check that the needle holder(422) and the needle release spring(435) are installed in a state in which the needle(30) can be removed. Therefore, it is possible to prevent a problem in which the applicator(10) is shipped from a factory in an inoperable state.

The needle separation unit(400) may be coupled to the plunger(300) in two assembled states.

For example, as shown in FIG. 9, the needle separation unit(400) may be coupled to the plunger(300) in an elastically deformed state such that the needle separation spring (435) applies an elastic force to the needle holder(422). In this case, in the course of assembling the needle separation unit(400), the needle holder(422) to which the needle separation spring(435) is connected is moved toward one end of the support column(410) so that the stopper(431) of the needle holder(422) can be inserted into the locking groove (414) of the support column(410). At this time, as the stopper(431) is caught on the snagging protuberance(415) of the support column(410), the needle holder(422) may be fixed in a state in which the needle separation spring(435) is tensioned. In addition, the needle separation unit(400) may be assembled to the plunger(300) in a state in which the needle separation spring(435) is elastically deformed.

As another example, as shown in FIG. 10, the needle separation unit(400) may be coupled to the plunger(300) in a state in which the needle separation spring(435) is not elastically deformed. In this case, after coupling the needle separation unit(400) to the plunger 300, the needle holder (422) can be simply moved to an operable position by using a separate jig(50) or the like. That is, when the trigger(428) of the needle separation unit(400) is pushed toward the sensor receiving portion(320) of the plunger(300) using a jig(50) or the like, the needle holder(422) may moves while tensioning the needle separation spring(435). When the stopper(431) is inserted into the locking groove(414) of the support column(410) while the needle holder(422) is moving, the stopper(431) is caught on the snagging protuberance (415) so that the needle holder(422) the needle holder(422) may be fixed while the needle separation spring(435) is tensioned.

When the needle holder(422) is moved to an operable position using a jig(50) in a state where the needle separation unit(400) is coupled to the plunger(300), the user may insert the end of the jig(50) into the slit(413) of the support column(410) from the outside of the support column(410). In addition, by moving the jig(50) along the slit(413), the needle holder(422) may be pushed to a position where the stopper(431) is caught on the snagging protuberance(415).

Hereinafter, a process of attaching the body attachable unit(20) to the user's body(B) using the applicator(10) for a continuous blood glucose measurement apparatus according to an embodiment of the present disclosure will be described.

First, as shown in FIG. 11, the protective cap(200) is separated. In the process of separating the protective cap (200), the release paper of the body attachable unit(20) is separated along with the protective cap(200), and the adhesive tape(22) of the body attachable unit(20) may be exposed.

Thereafter, as shown in FIG. 12, the applicator(10) is positioned on the body(B) of the user, and the press button (140) is pressed. When the press button(140) is operated, as the shooting plate(130) moves, the fixing force of the plunger(300) fixed at the first position(P1) is released. When the fixing force of the plunger(300) by the shooting plate (130) is released, as shown in FIG. 13, the plunger(300) to which the body attachable unit(20) is mounted moves toward the second position(P2) by the plunger spring(340), and the needle(30) and then the sensor unit(21) of the body attaching unit(20) penetrate the user's skin and are inserted into the body(B).

As shown in FIG. 14, while the plunger(300) moves to the second position(P2), when the trigger(428) of the needle separation unit(400) reaches the pressing portion(125) of the main case(100), the trigger inclined portion(429) of trigger (428) moves toward the user's body(B) in a state in contact with the pressing inclined portion(126) of the body portion (411). At this time, as the pressing portion(125) presses the trigger(428), the holder wing(426) of the needle holder(422) is elastically deformed and closed. As the holder wing(426) is elastically deformed in this way, the stopper(431) of the holder wing(426) escapes from the locking groove(414) of the support column(410). When the stopper(431) is out of the locking groove(414), the fixing force on the needle holder(422) is released, the needle holder(422) is pulled away from the user's body(B) by the elastic force of the needle separation spring(435).

As the needle holder(422) moves by the elastic force of the needle separation spring(435), the needle(30) inserted into the body(B) together with the sensor unit(21) of the body attachable unit(20) is pulled by the needle holder(422) and detached from the body attachable unit(20).

Subsequently, as shown in FIG. 15, the plunger(300) moves to the second position(P2) by the elastic force of the plunger spring(340) and then stops. At this time, the body attachable unit(20) is attached to the user's body(B) by the adhesive tape(22).

While the body attachable unit(20) moves to the second position(P2), a time point at which the needle holder(422) separates the needle(30) from the body attachable unit(20) may be set to an appropriate time point after the needle(30) penetrates the skin of the user's body(B) and guides the sensor unit(21) to be inserted into the user's body(B). For it, the pressing portion(125) may be disposed at an appropriate position in the movement path of the needle holder(422) according to the length of the needle(30) and so on.

As shown in FIG. 16, after the body attachable unit(20) is attached to the user's body(B), when the applicator(10) is separated from the body attachable unit(20), the attachment operation of the body attachable unit(20) is completed.

Then, the body attachable unit(20) may measure the user's blood sugar and transmit the measurement information to the external terminal(40).

Although the preferred embodiments have been described above, the scope of the present disclosure is not limited to the forms described and illustrated above.

For example, although the drawing shows that the needle separation spring(435) of the needle separation unit(400) has a tension spring structure, the needle separation spring may have a compression spring structure to apply elastic force to the needle holder(422).

In addition, although it was described above that the body attachable unit attached to the user's body by the applicator has a function of measuring blood sugar and transmitting the measurement data, the body attachable unit may have a configuration in which a sensor unit for measuring blood sugar is coupled to a base equipped with an adhesive tape. In this case, after the body attachable unit is attached to the user's body, a separate transmitter for data transmission may be coupled to the base of the body attachable unit.

In the above, the disclosure has been shown and described with respect to preferred embodiments to illustrate the principles of the disclosure, but the present disclosure is not limited to the configuration and operation as shown and described. Rather, it should be appreciated by those skilled in the art that various changes and modifications can be made to the present disclosure without departing from the spirit and scope of the appended claims.

What is claimed is:

1. An applicator for a continuous blood glucose measurement apparatus to operate to attach a body attachable unit having a sensor unit inserted into a body of a user for measuring blood glucose, the applicator comprising:
a main case;
a plunger separably coupled to the body attachable unit, and installed to be movable from a first location to a second location inside the main case to discharge the body attachable unit in a direction of an outside of the main case;
a needle separably coupled to the body attachable unit to be inserted into the body of the user together with the sensor unit;
a needle separation unit configured to move the needle in a direction opposite to a discharged direction of the plunger to separate the needle from the body of the user, wherein the needle separation unit comprises a locking part, and the locking part is configured to be assembled to the plunger in a way in which the locking part engages with one side of the plunger, wherein the needle separation unit comprises: a support column having the locking part, a needle holder movably coupled to the support column to be coupled to one end of the needle, and a needle separation spring configured to apply an elastic force to the needle holder in a direction of separating the needle from the body of the user, and wherein the support column is configured to be assembled to the plunger by forming an assembly together with the needle holder and the needle separation spring;
a support column hook to which one end of the needle separation spring is connected is provided inside the support column,
the needle holder comprises a needle holder hook to which another end of the needle separation spring is connected, and
the needle separation spring is configured to apply the elastic force to the needle holder so that the needle holder is pulled toward the support column hook.

2. The applicator for the continuous blood glucose measurement apparatus according to claim 1, wherein
the support column comprises
a body portion to which the needle holder and the needle separation spring are coupled, and
wherein the locking part is provided at one end of the body portion.

3. The applicator for the continuous blood glucose measurement apparatus according to claim 2, wherein
the locking part is elastically and deformably connected to the body portion.

4. The applicator for the continuous blood glucose measurement apparatus according to claim 3, wherein
the plunger comprises a fixing part configured to be engageable with the locking part, and
one of the locking part and the fixing part has a coupling groove, and a remaining one of the locking part and the fixing part has a fixing protrusion configured to be insertable into the coupling groove.

5. The applicator for the continuous blood glucose measurement apparatus according to claim 1, wherein
the needle holder comprises
a holder head to which one end of the needle is coupled,
a holder wing comprising a wing body elastically and deformably connected to the holder head and a stopper protruding from the wing body,
the support column comprises a snagging protuberance with which the stopper is engageable, and
a pressing portion configured to elastically deform the holder wing such that the stopper is disengaged from the snagging protuberance is provided inside the main case.

6. The applicator for the continuous blood glucose measurement apparatus according to claim 5, wherein
the holder wing protrudes from the wing body and includes a trigger in which a protruded height from the wing body is greater than a height of the stopper protruded from the wing body,
the support column comprises a slit formed in a longitudinal direction of the support column to allow the trigger to be inserted, and
the pressing portion is arranged on a movement path of the needle holder to elastically deform the holder wing by pressing the trigger while the plunger moves from the first location to the second location.

7. The applicator for the continuous blood glucose measurement apparatus according to claim 1, wherein
the needle separation unit is configured to be assembled to the plunger in an elastically deformed state such that the needle separation spring applies the elastic force to the needle holder.

8. The applicator for the continuous blood glucose measurement apparatus according to claim 1, wherein
the needle separation unit is configured to be assembled to the plunger in a state in which the needle separation spring is not elastically deformed.

9. An applicator for a continuous blood glucose measurement apparatus to operate to attach a body attachable unit having a sensor unit inserted into a body of a user for measuring blood glucose, the applicator comprising:
a main case;
a plunger separably coupled to the body attachable unit, and installed to be movable from a first location to a second location inside the main case to discharge the body attachable unit in a direction of an outside of the main case, the plunger comprises a fixing part engaged with the locking part, and wherein one of the locking part and the fixing part has a coupling groove, and a remaining one of the locking part and the fixing part has a fixing protrusion configured to be insertable into the coupling groove;
a needle separably coupled to the body attachable unit to be inserted into the body of the user together with the sensor unit;
a needle separation unit including a support column fixedly engaged with the plunger body, and configured to move the needle in a direction opposite to a discharged direction of the plunger to separate the needle from the body of the user, wherein the support column comprises: a body portion; and a locking part provided at a lower end portion of the body portion to engage the body portion with the plunger body, and the needle separation unit further includes: a needle holder 5 coupled to one end of the needle and movably coupled to inside of the support column; and a needle separation spring disposed between the needle holder and a top end portion of the inside of the support column, and configured to apply an elastic force to the needle holder 10 in a direction of separating the needle from the body of the user.

\*   \*   \*   \*   \*